US009314221B2

(12) United States Patent
Katcha et al.

(10) Patent No.: US 9,314,221 B2
(45) Date of Patent: Apr. 19, 2016

(54) COMMON DC BUS POWER CT SYSTEM

(71) Applicant: General Electric Company, Schenectady, NY (US)

(72) Inventors: Jason Stuart Katcha, Waukesha, WI (US); Ezana T. Mekonnen, Waukesha, WI (US)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 254 days.

(21) Appl. No.: 13/959,248

(22) Filed: Aug. 5, 2013

(65) Prior Publication Data

US 2015/0036786 A1  Feb. 5, 2015

(51) Int. Cl.
| | |
|---|---|
| *A61B 6/00* | (2006.01) |
| *A61B 6/03* | (2006.01) |
| *A61B 8/00* | (2006.01) |
| *H02P 3/14* | (2006.01) |

(52) U.S. Cl.
CPC ... *A61B 6/56* (2013.01); *A61B 6/03* (2013.01); *A61B 6/032* (2013.01); *A61B 8/56* (2013.01); *A61B 6/035* (2013.01); *H02P 3/14* (2013.01); *Y10T 29/49002* (2015.01)

(58) Field of Classification Search
CPC .............................. A61B 6/032; A61B 6/035
See application file for complete search history.

(56) References Cited

U.S. PATENT DOCUMENTS

| | | | |
|---|---|---|---|
| 7,522,705 B2 | 4/2009 | Katcha et al. | |
| 2009/0060122 A1* | 3/2009 | Kasuya | ........................... 378/15 |
| 2012/0027161 A1* | 2/2012 | Abenaim et al. | .................. 378/4 |
| 2012/0109515 A1* | 5/2012 | Uyeki et al. | .................. 701/423 |

FOREIGN PATENT DOCUMENTS

WO    2013015791 A1    1/2013

OTHER PUBLICATIONS

International Search Report and Written Opinion for corresponding PCT application No. PCT/US2014/048634 dated Oct. 31, 2014; 7 pages.

\* cited by examiner

*Primary Examiner* — Hoon Song
(74) *Attorney, Agent, or Firm* — Fletcher Yoder, P.C.

(57) ABSTRACT

A CT system includes a gantry having a rotatable base and having an opening for receiving an object to be scanned, and an AC-to-DC converter coupleable to a 3-phase AC facility power, and coupled through a DC bus to a gantry motor to rotationally drive the rotatable base using DC power from the AC-to-DC converter. Rotational energy in the rotatable base is converted to DC electrical energy in the gantry motor during gantry braking, and provided to the DC bus.

20 Claims, 3 Drawing Sheets

COMMON DC BUS POWER CT SYSTEM

BACKGROUND

This disclosure relates generally to diagnostic imaging and, more particularly, to improved energy management for a computed tomography (CT) system.

Typically, in computed tomography (CT) imaging systems, an x-ray source emits a fan or cone-shaped beam toward a subject or object, such as a patient or a piece of luggage. Hereinafter, the terms "subject" and "object" shall include anything capable of being imaged. The beam, after being attenuated by the subject, impinges upon an array of radiation detectors. The intensity of the attenuated beam radiation received at the detector array is typically dependent upon the attenuation of the x-ray beam by the subject. Each detector element of the detector array produces a separate electrical signal indicative of the attenuated beam received by each detector element. The electrical signals are transmitted to a data processing system for analysis which ultimately produces an image.

Generally, the x-ray source and the detector array are rotated about the gantry within an imaging plane and around the subject. X-ray sources typically include x-ray tubes, which emit the x-ray beam at a focal point. X-ray detectors typically include a collimator for collimating x-ray beams received at the detector, a scintillator for converting x-rays to light energy adjacent the collimator, and photodiodes for receiving the light energy from the adjacent scintillator and producing electrical signals therefrom. Typically, each scintillator of a scintillator array converts x-rays to light energy. Each scintillator discharges light energy to a photodiode adjacent thereto. Each photodiode detects the light energy and generates a corresponding electrical signal. The outputs of the photodiodes are transmitted to the data processing system for image reconstruction. Imaging data may be obtained using x-rays that are generated at a single polychromatic energy. However, some systems may obtain multi-energy images that provide additional information for generating images.

When the gantry is rotated, it includes a significant amount of rotational kinetic energy that is typically dissipated in a device such as an electrical resistor. That is, the gantry is braked and the rotational energy of the gantry is converted to electrical energy and dissipated as heat in the electrical resistor. In recent years, gantry speeds have increased to provide improved temporal resolution in CT imaging. As such, the amount of dissipated electrical energy that is lost when braking the gantry has increased substantially.

The amount of energy stored in a rotating body is generally a function of its rotational velocity squared. Thus, as gantry speeds have increased over the years from, for example, from 1 to 3 Hz, the amount of energy available and expended in each braking event has significantly increased as well. In addition the amount of rotating mass has increased over this period. Power of the x-ray tube has increased (average and peak power), detector coverage has increased, and the voltage capability of the generator has increased, as examples. These increases have resulted in larger x-ray tubes, detectors, generators, and heat exchangers, as examples. G-loading increases as a function of gantry rotational velocity squared, as well. Thus, the mass of support structure of the rotating portion of the gantry itself has increased over time to maintain acceptably small component deflections during gantry operation.

All of these trends toward larger components, faster gantry speed, and increased mass of the rotating support structure have led to an increased amount of energy to be dissipated during gantry braking events. As a result, the capability of the dissipating resistor itself has increased in size, leading to greater cost as well. Further, it is expected that gantry speeds will only continue to increase to further improve temporal resolution, to perhaps 5 Hz and faster.

As such, these trends in CT lead to an increasing amount of rotational kinetic energy that is lost when the rotating system is braked, and it is therefore increasingly desirable to recover the energy for useful purposes. A gantry typically includes an uninterruptible power supply (UPS) that provides 3-phase power to a 3-phase transformer. Power is split out from the transformer in various sub-circuits to provide power to: a high voltage generator via an AC-DC converter (to power the x-ray tube with DC power); an axial drive and motor for rotating the gantry with 3-phase power (typically 480 VAC 3-phase); and to power other system electronics (typically 120 VAC 3-phase). In such systems, power flows generally only in one direction, and energy recoverable from the CT gantry cannot be used without additional hardware.

One known system for recovering CT rotational energy includes additional AC/DC and DC/AC converters and an additional battery. This known system therefore includes additional hardware and control operation complexity to enable recovery of the gantry energy, which leads to overall system cost and design complexity.

Therefore, it would be desirable to have an overall cost effective method and apparatus to improve energy management in a CT system.

BRIEF DESCRIPTION

Embodiments are directed toward a method and apparatus to improved energy management in a CT system.

According to one aspect, a CT system includes a gantry having a rotatable base and having an opening for receiving an object to be scanned, and an AC-to-DC converter coupleable to a 3-phase AC facility power, and coupled through a DC bus to a gantry motor to rotationally drive the rotatable base using DC power from the AC-to-DC converter. Rotational energy in the rotatable base is converted to DC electrical energy in the gantry motor during gantry braking, and provided to the DC bus.

According to another aspect, a method of manufacturing a CT system includes electrically coupling a gantry motor to a DC electrical bus, wherein the gantry motor is mechanically coupled to a rotatable gantry of the CT system, electrically coupling a DC output of an AC-to-DC converter to the DC bus electrical bus, wherein an AC input to the AC-to-DC converter is coupleable to a 3-phase AC facility power, wherein rotational energy in the rotatable gantry is converted to DC electrical energy in the gantry motor during gantry braking, and provided to the DC bus.

According to yet another aspect, an imaging system electrical circuit includes an electrical bus, a DC output of an AC-to-DC converter coupled to the electrical bus, and a gantry motor electrically coupled to the electrical bus. An AC input to the AC-to-DC converter is coupleable to a 3-phase AC electrical source, and rotational energy in a gantry that is mechanically coupled to the gantry motor is converted to DC electrical energy in the gantry motor during gantry braking, and provided to the electrical bus.

Various other features and advantages will be made apparent from the following detailed description and the drawings.

DETAILED DESCRIPTION

The operating environment of disclosed embodiments is described with respect to a sixty-four-slice computed tomography (CT) system. However, it will be appreciated by those skilled in the art that embodiments are equally applicable for use with other multi-slice configurations. Moreover, disclosed embodiments will be described with respect to the detection and conversion of x-rays. However, one skilled in the art will further appreciate that embodiments are equally applicable for the detection and conversion of other high frequency electromagnetic energy. Disclosed embodiments will be described with respect to a "third generation" CT scanner, but is equally applicable with other CT systems as well as vascular and surgical C-arm systems and other x-ray tomography systems.

Figure 1:
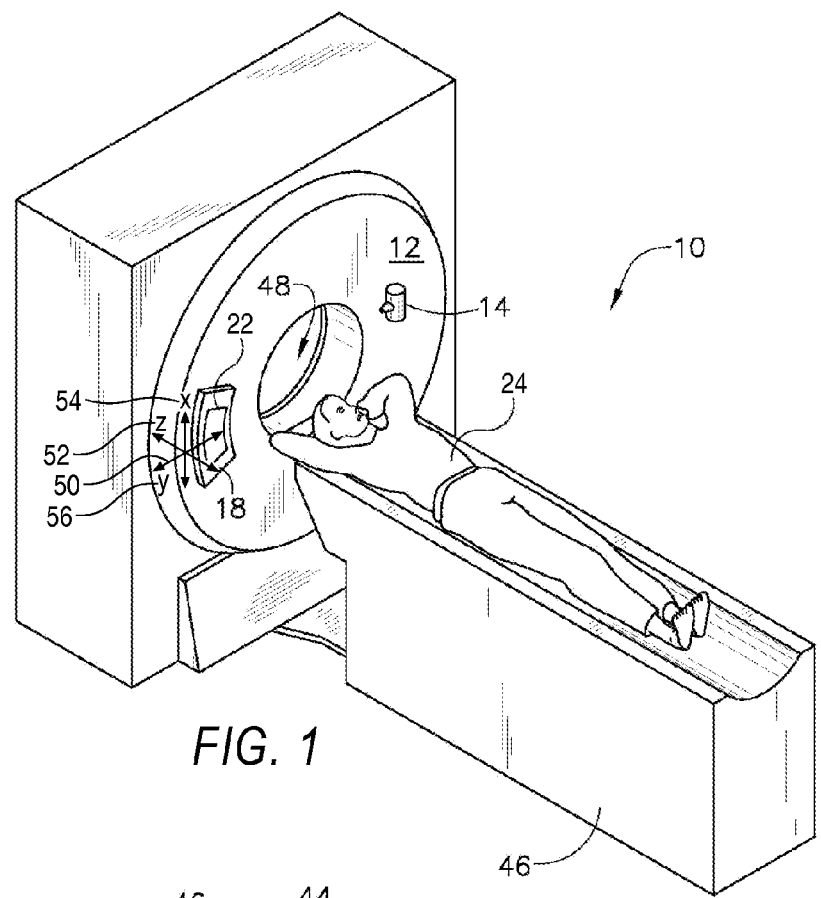
FIG. 1 is a pictorial view of a CT imaging system that incorporates disclosed embodiments.
Figure 2:
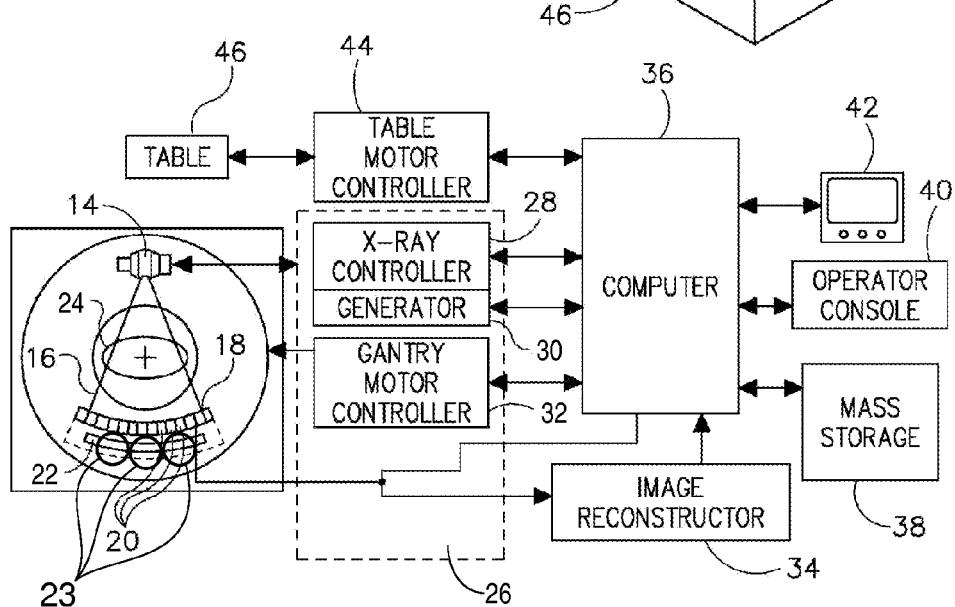
FIG. 2 is a block schematic diagram of the system illustrated in FIG. 1.

Referring to FIGS. 1 and 2, a computed tomography (CT) imaging system 10 is shown as including a gantry 12 representative of a "third generation" CT scanner. Gantry 12 has an x-ray source 14 that projects a beam of x-rays 16 toward a detector assembly or collimator 18 on the opposite side of the gantry 12. X-ray source 14 includes either a stationary target or a rotating target. Detector assembly 18 is formed by a plurality of detectors 20 data acquisition systems (DAS) 22, and fans 23. The plurality of detectors 20 sense the projected x-rays that pass through a medical patient 24, and DAS 22 converts the data to digital signals for subsequent processing. Each detector 20 produces an analog electrical signal that represents the intensity of an impinging x-ray beam and hence the attenuated beam as it passes through patient 24. During a scan to acquire x-ray projection data, gantry 12 and the components mounted thereon rotate about a center of rotation.

Rotation of gantry 12 and the operation of x-ray source 14 are governed by a control mechanism 26 of CT system 10. Control mechanism 26 includes an x-ray controller 28 and generator 30 that provides power and timing signals to x-ray source 14 and a gantry motor controller 32 that controls the rotational speed and position of gantry 12. An image reconstructor 34 receives sampled and digitized x-ray data from DAS 22 and performs high speed image reconstruction. The reconstructed image is applied as an input to a computer 36 which stores the image in a mass storage device 38.

Computer 36 also receives commands and scanning parameters from an operator via an operator console 40 that has some form of operator interface, such as a keyboard, mouse, voice activated controller, or any other suitable input apparatus. An associated display 42 allows the operator to observe the reconstructed image and other data from computer 36. The operator supplied commands and parameters are used by computer 36 to provide control signals and information to DAS 22, x-ray controller 28, and gantry motor controller 32. In addition, computer 36 operates a table motor controller 44 which controls a motorized table 46 to position patient 24 and gantry 12. Particularly, table 46 moves patients 24 through a gantry opening 48 in whole or in part. A coordinate system 50 for detector assembly 18 defines a patient or Z-axis 52 along which patient 24 is moved in and out of opening 48, a gantry circumferential or X-axis 54 along which detector assembly 18 passes, and a Y-axis 56 that passes along a direction from a focal spot of X-ray source 14 to detector assembly 18.

X-ray source 14, in accordance with present embodiments, is configured to emit x-rays or x-ray beam 16 at one or more energies. For example, x-ray source 14 may be configured to switch between relatively low energy polychromatic emission spectra (e.g., at approximately 80 kVp) and relatively high energy polychromatic emission spectra (e.g., at approximately 140 kVp). As will be appreciated, x-ray source 14 may also be operated so as to emit x-rays at more than two different energies. Similarly, x-ray source 14 may emit at polychromatic spectra localized around energy levels (i.e., kVp ranges) other than those listed herein (e.g., 100 kVP, 120 kVP, etc.). Selection of the respective energy levels for emission may be based, at least in part, on the anatomy being imaged.

In some embodiments X-ray controller 28 may be configured to selectively activate x-ray source 14 such that tubes or emitters at different locations within system 10 may be operated in synchrony with one another or independent of one another. In certain embodiments discussed herein, the x-ray controller 28 may be configured to provide fast-kVp switching of x-ray source 14 so as to rapidly switch source 14 to emit X-rays at the respective polychromatic energy spectra in succession during an image acquisition session. For example, in a dual-energy imaging context, x-ray controller 28 may operate x-ray source 14 so that x-ray source 14 alternately emits x-rays at the two polychromatic energy spectra of interest, such that adjacent projections are acquired at different energies (i.e., a first projection is acquired at high energy, the second projection is acquired at low energy, the third projection is acquired at high energy, and so forth). In one such implementation, fast-kVp switching operation performed by x-ray controller 28 yields temporally registered projection data. In some embodiments, other modes of data acquisition and processing may be utilized. For example, a low pitch helical mode, rotate-rotate axial mode, N×M mode (e.g., N low-kVp views and M high-kVP views) may be utilized to acquire dual-energy datasets.

Figure 3:
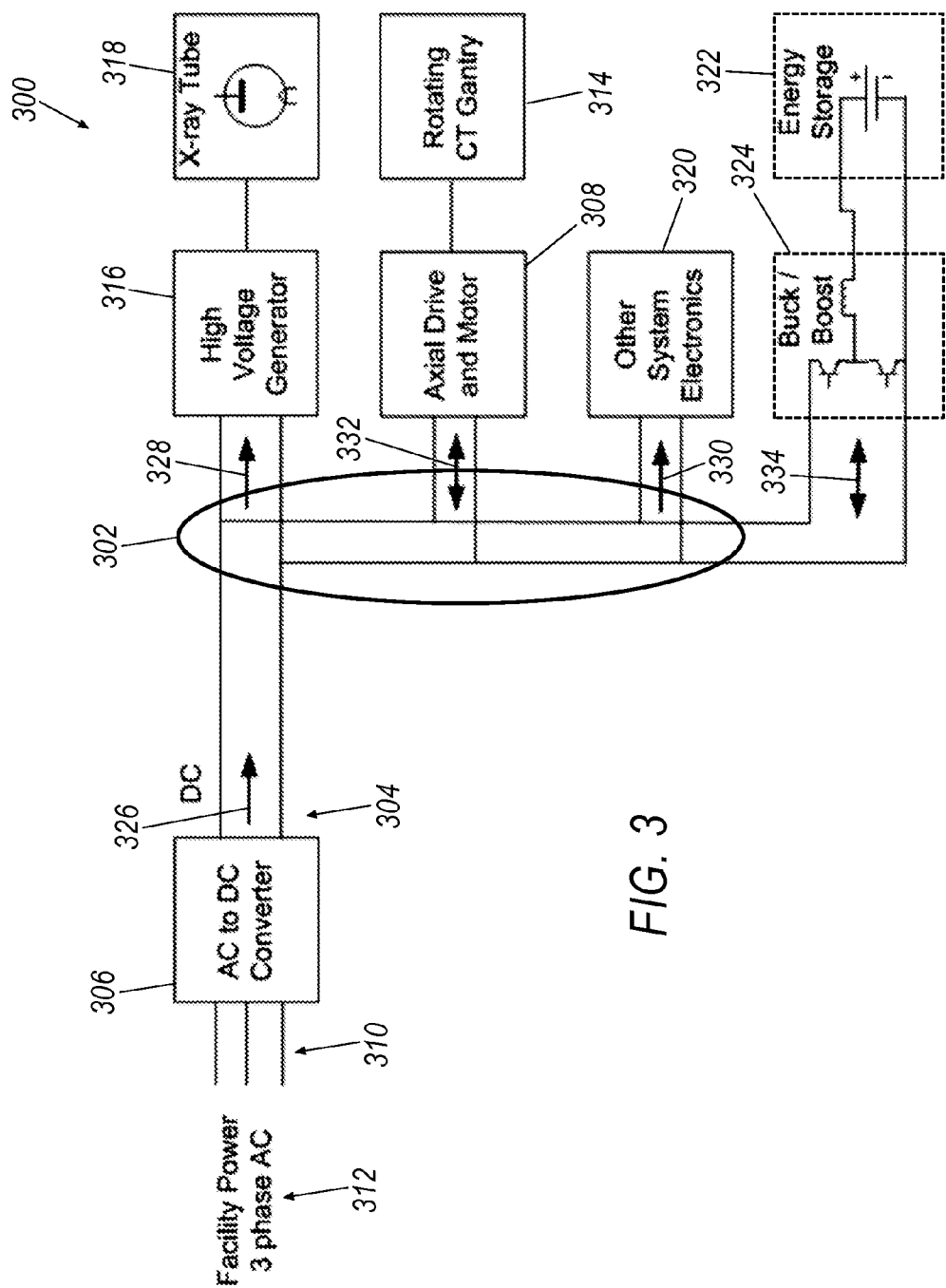
FIG. 3 is an imaging system electrical circuit that is incorporated into system 10 shown in FIGS. 1 and 2.
Figure 4:
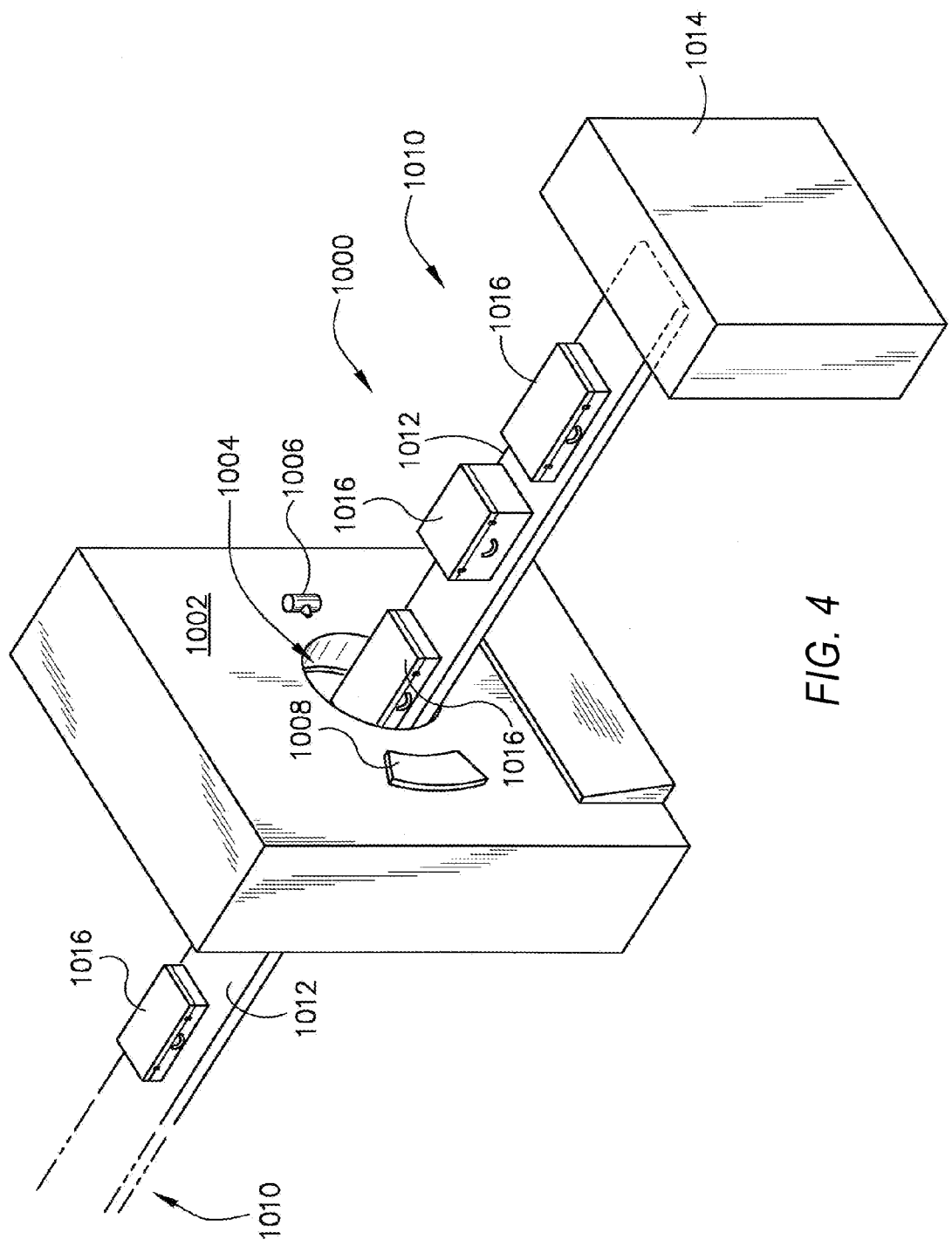
FIG. 4 is a pictorial view of a CT system for use with a non-invasive package inspection system according to an embodiment.

Referring to FIG. 3, an imaging system electrical circuit 300 is illustrated that is incorporated into system 10 shown in FIGS. 1 and 2. Circuit 300 includes a DC or electrical bus 302 coupled to a DC output 304 of an AC-to-DC converter 306. An axial drive and gantry motor 308 is electrically coupled to the electrical bus. An AC input 310 to the AC-to-DC converter is coupleable to a 3-phase AC electrical source 312. A gantry 314 (similar to gantry 12 of FIGS. 1 and 2) is mechanically coupled to gantry motor 308 (similar to gantry motor controller 32 of FIG. 2), and rotational energy in rotating gantry is regeneratively converted to DC electrical energy in gantry motor 308 during gantry braking, and the DC electrical energy is provided to the electrical bus.

Circuit 300 includes a high-voltage generator 316 (similar to generator 30 of FIG. 2) coupled to electrical bus 302. High-voltage generator 316 is configured to provide power to an x-ray tube 318 (similar to x-ray tube 14 of FIGS. 1 and 2). Circuit 300 includes one or more components 320 coupled to electrical bus 302, the one or more components 320 including, as examples and consistent with FIGS. 1 and 2, a data acquisition system (DAQ) 22, a detector cooling fan 23, and a system control computer 36. The one or more components 320 are powered by the DC electrical energy converted from the rotational energy in the rotatable base that is converted in gantry motor 308, and passed to bus 302.

In an optional embodiment, circuit 300 includes an energy storage device 322 coupled to bus 302, and in one example energy storage device 322 is a lithium ion battery having a higher energy density and peak power capability than conventional batteries. Further, energy storage device 322 is coupled via a voltage stepping device to a buck-boost converter 324 that is coupled between the energy storage device 322 and bus 302. Typically, a buck-boost converter such as converter 324 operates as a DC stepper to step up the DC voltage in one direction and step down the voltage in the other direction. In this case, DC bus 302 includes a voltage sufficient to power the generator 316, gantry motor 308, and other electrical components 320. Buck-boost converter may therefore be appropriately used to step up and down, accordingly, per the voltage on bus 302 and per the operating voltage of energy storage 322.

In one embodiment, however, circuit 300 does not include an energy storage unit, such as energy storage 322 (or converter 324) coupled to bus 302. Thus, in the embodiment without energy storage 322, system design and operation is simpler and is a less expensive alternative. However, because no energy is stored, then the regenerative energy from the rotating gantry is provided directly to either high voltage generator 316, other components 320, or is dissipated and lost. Thus, whether circuit 300 includes optional energy storage 322 may depend on a cost tradeoff for the additional functionality of energy storage and additional system complexity, versus the ability to recover cost to extent as lost energy. Further, energy storage 322 can further provide additional power to the system during interruptions in power supply, thus serving as an uninterruptible power supply (UPS).

In operation, 3-phase AC facility power is provided from source 312, and in one embodiment is 480 VAC at 150 KW. The power is converted to DC power in converter 306 and passed as DC output 304 as DC electrical power 326. DC electrical power 326 is thereby provided to bus 302, through which the power may be distributed the various system components as described. DC power may pass 328 to high voltage generator 316, or may pass 330 to other system electronics 320. DC power may also pass 332, 334 to gantry motor 308 and energy storage 322, respectively, but as illustrated 332, 334 power may pass in both directions based on the mode of operation. That is, when powering gantry motor 308, power may pass to motor 308 from bus 302, but when operating in regenerative mode power may pass from motor 308 to bus 302. Similarly, power may pass 334 from bus 302 to storage 322, or power may pass from storage 322 to bus 302. In either case, when power is passing from gantry 314 and/or storage 322, then energy is passed to either generator 316 or other system electronics 320.

As such, circuit 300 illustrates a circuit in which power may be provided as DC power from an AC 3-phase source, but to save cost and reclaim energy that may otherwise be lost in a conventional operation, energy from the rotating gantry may be reclaimed and stored or consumed in other system components. In one example, a gantry rotating at high speed may contain approximately 150 kJ or energy which provides 12 kW of energy if dissipated within a 50 second period. Of course it is contemplated that such energy output is not constant, but generally an average over the period of time and as one example to express the amount of possible energy savings. Circuit 300 therefore provides an ability to reclaim lost energy while reducing or eliminating the need for a bulky and costly resistive device that is typically provided in a system for power dissipation.

Circuit 300 may be incorporated into CT system architecture, such as system 10 illustrated in FIGS. 1 and 2. Thus, CT system 10 includes a gantry 314 having a rotatable base and having an opening for receiving an object to be scanned. AC-to-DC converter 306 is couplable to a 3-phase AC facility power 312, and coupled through DC bus 302 to a gantry motor 308 to rotationally drive the rotatable base using DC power 326 from AC-to-DC converter 306. Rotational energy in the rotatable base of gantry 314 is converted to DC electrical energy in the gantry motor 308 during gantry braking, and provided to DC bus 302.

Correspondingly, disclosed herein is a method of manufacturing a CT system that includes electrically coupling a gantry motor to a DC electrical bus. The gantry motor is mechanically coupled to a rotatable gantry of the CT system. The method includes electrically coupling a DC output of an AC-to-DC converter to the DC bus electrical bus, wherein an AC input to the AC-to-DC converter is couplable to a 3-phase AC facility power. Rotational energy in the rotatable gantry is converted to DC electrical energy in the gantry motor during gantry braking, and provided to the DC bus.

Referring now to FIG. 6, there is shown a package/baggage inspection system 1000 that can use the image acquisition and reconstructions techniques according to embodiments disclosed and which includes a rotatable gantry 1002 having an opening 1004 therein through which packages or pieces of baggage may pass. The rotatable gantry 1002 houses one or more x-ray energy sources 1006 as well as a detector assembly 1008 having scintillator arrays comprised of scintillator cells. A conveyor system 1010 is also provided and includes a conveyor belt 1012 supported by structure 1014 to automatically and continuously pass packages or baggage pieces 1016 through opening 1004 to be scanned. Objects 1016 are passed through opening 1004 by conveyor belt 1012, imaging data is then acquired, and the conveyor belt 1012 removes the packages 1016 from opening 1004 in a controlled and continuous manner. As a result, postal inspectors, baggage handlers, and other security personnel may non-invasively inspect the contents of packages 1016 for explosives, knives, guns, contraband, etc.

An implementation of system 10 and/or 1000 in an example comprises a plurality of components such as one or more of electronic components, hardware components, and/or computer software components. A number of such components can be combined or divided in an implementation of the system 10 and/or 1000. An exemplary component of an implementation of the system 10 and/or 1000 employs and/or comprises a set and/or series of computer instructions written in or implemented with any of a number of programming languages, as will be appreciated by those skilled in the art. An implementation of system 10 and/or 1000 in an example comprises any (e.g., horizontal, oblique, or vertical) orientation, with the description and figures herein illustrating an exemplary orientation of an implementation of the system 10 and/or 1000, for explanatory purposes.

An implementation of system 10 and/or system 1000 in an example employs one or more computer readable signal bearing media. A computer-readable signal-bearing medium in an example stores software, firmware and/or assembly language for performing one or more portions of one or more implementations. An example of a computer-readable signal-bearing medium for an implementation of the system 10 and/or the system 1000 comprises the recordable data storage medium of the image reconstructor 34, and/or mass storage device 38 of computer 36. A computer-readable signal-bearing medium for an implementation of the system 10 and/or the system 1000 in an example comprises one or more of a magnetic, electrical, optical, biological, and/or atomic data storage medium. For example, an implementation of the computer-readable signal-bearing medium comprises floppy disks, magnetic tapes, CD-ROMs, DVD-ROMs, hard disk drives, and/or electronic memory. In another example, an implementation of the computer-readable signal-bearing medium comprises a modulated carrier signal transmitted over a network comprising or coupled with an implementation of the system 10 and/or the system 1000, for instance, one or more of a telephone network, a local area network ("LAN"), a wide area network ("WAN"), the Internet, and/or a wireless network.

As such, CT system power architecture is improved by powering components from a common DC bus. This allows use of energy recovered from gantry deceleration without additional hardware. Further, in the embodiment in which the energy storage device is provided, the storage device can be used as a low cost UPS. A common DC bus powers most or all CT Subsystems. Facility power is rectified with an AC/DC converter which may optionally contain an isolation transformer. The output on the converter is the common DC bus that is connected to most or all sub-systems.

The axial drive motor, which drives the CT gantry rotation is also powered from the common DC bus. When the gantry is decelerated, the energy in the gantry is recovered by the axial drive and is delivered to the DC bus where it can be used by other system electronics connected to the DC bus. A battery or other energy storage device can be connected to the DC bus through a buck-boost converter which controls the power flow into and out of the DC bus. The battery can be used for peak power shaving or as a UPS. Energy is thereby recovered from the gantry without additional conversion hardware.

According to one embodiment, a CT system includes a gantry having a rotatable base and having an opening for receiving an object to be scanned, and an AC-to-DC converter coupleable to a 3-phase AC facility power, and coupled through a DC bus to a gantry motor to rotationally drive the rotatable base using DC power from the AC-to-DC converter. Rotational energy in the rotatable base is converted to DC electrical energy in the gantry motor during gantry braking, and provided to the DC bus.

According to another embodiment, a method of manufacturing a CT system includes electrically coupling a gantry motor to a DC electrical bus, wherein the gantry motor is mechanically coupled to a rotatable gantry of the CT system, electrically coupling a DC output of an AC-to-DC converter to the DC bus electrical bus, wherein an AC input to the AC-to-DC converter is coupleable to a 3-phase AC facility power, wherein rotational energy in the rotatable gantry is converted to DC electrical energy in the gantry motor during gantry braking, and provided to the DC bus.

According to yet another embodiment, an imaging system electrical circuit includes an electrical bus, a DC output of an AC-to-DC converter coupled to the electrical bus, and a gantry motor electrically coupled to the electrical bus. An AC input to the AC-to-DC converter is coupleable to a 3-phase AC electrical source, and rotational energy in a gantry that is mechanically coupled to the gantry motor is converted to DC electrical energy in the gantry motor during gantry braking, and provided to the electrical bus.

When introducing elements of various embodiments, the articles "a," "an," "the," and "said" are intended to mean that there are one or more of the elements. The terms "comprising," "including," and "having" are intended to be inclusive and mean that there may be additional elements other than the listed elements. Furthermore, any numerical examples in the following discussion are intended to be non-limiting, and thus additional numerical values, ranges, and percentages are within the scope of the disclosed embodiments.

While the preceding discussion is generally provided in the context of medical imaging, it should be appreciated that the present techniques are not limited to such medical contexts. The provision of examples and explanations in such a medical context is to facilitate explanation by providing instances of implementations and applications. The disclosed approaches may also be utilized in other contexts, such as the non-destructive inspection of manufactured parts or goods (i.e., quality control or quality review applications), and/or the non-invasive inspection of packages, boxes, luggage, and so forth (i.e., security or screening applications).

While the disclosed subject matter has been described in detail in connection with only a limited number of embodiments, it should be readily understood that the disclosure is not limited to such disclosed embodiments. Rather, that disclosed can be modified to incorporate any number of variations, alterations, substitutions or equivalent arrangements not heretofore described, but which are commensurate with the spirit and scope of the disclosure. Furthermore, while single energy and dual-energy techniques are discussed above, that disclosed encompasses approaches with more than two energies. Additionally, while various embodiments have been described, it is to be understood that disclosed aspects may include only some of the described embodiments. Accordingly, that disclosed is not to be seen as limited by the foregoing description, but is only limited by the scope of the appended claims.

What is claimed is:

1. A CT system comprising:
    a gantry having a rotatable base and having an opening for receiving an object to be scanned;
    an AC-to-DC converter coupleable to a 3-phase AC facility power, and coupled through a DC bus to a gantry motor to rotationally drive the rotatable base using DC power from the AC-to-DC converter, wherein rotational energy in the rotatable base is converted to DC electrical energy in the gantry motor during gantry braking, and provided to the DC bus; and
    an energy storage system coupled to the DC bus, wherein the energy storage system is configured to provide power, via the DC bus, to an additional component of the CT system.

2. The CT system of claim 1, wherein the energy storage system comprises an energy storage device coupled to the DC bus.

3. The CT system of claim 2, wherein the energy storage device is a lithium ion battery.

4. The CT system of claim 1, wherein the energy storage system comprises a buck-boost converter coupled between the energy storage device and the DC bus.

5. The CT system of claim 1, further comprising:
    an x-ray tube attached to the gantry; and
    a high-voltage generator coupled to the DC bus, the high-voltage generator configured to provide power to the x-ray tube.

6. The CT system of claim 1, wherein the additional component comprises at least one of a data acquisition system (DAQ), a detector cooling fan, and a system control computer, wherein the one or more components are powered by the DC electrical energy converted from the rotational energy in the rotatable base.

7. A method of manufacturing a CT system, comprising:
    electrically coupling a gantry motor to a DC electrical bus, wherein the gantry motor is mechanically coupled to a rotatable gantry of the CT system;
    electrically coupling a DC output of an AC-to-DC converter to the DC bus electrical bus, wherein an AC input to the AC-to-DC converter is coupleable to a 3-phase AC facility power, wherein rotational energy in the rotatable gantry is converted to DC electrical energy in the gantry motor during gantry braking, and provided to the DC bus; and electrically coupling an energy storage system to the DC bus, wherein the energy storage system is configured to provide power, via the DC bus, to an additional component of the CT system.

8. The method of claim 7, wherein electrically coupling the energy storage system comprises electrically coupling a battery storage device to the DC bus.

9. The method of claim 8, wherein coupling the battery storage device comprises coupling a lithium ion battery.

10. The method of claim 8, wherein electrically coupling the energy storage system comprises electrically coupling the battery storage device to the DC bus via a buck-boost converter that is coupled therebetween.

11. The method of claim 7, further comprising:
attaching an x-ray tube to the rotatable gantry; and
electrically coupling a high-voltage generator to the DC bus and to a DC electrical input of the x-ray tube.

12. The method of claim 7, wherein the additional component comprises at least one of a data acquisition system (DAQ), a detector cooling fan, and a system control computer, wherein the additional components are powered by the DC electrical energy converted from the rotational energy in the rotatable base.

13. An imaging system electrical circuit, comprising:
an electrical bus;
a DC output of an AC-to-DC converter coupled to the electrical bus;
a gantry motor electrically coupled to the electrical bus;
wherein:
an AC input to the AC-to-DC converter is coupleable to a 3-phase AC electrical source; and
rotational energy in a gantry that is mechanically coupled to the gantry motor is converted to DC electrical energy in the gantry motor during gantry braking, and provided to the electrical bus; and
an energy storage system coupled to the electrical bus, wherein the energy storage system is configured to provide power, via the DC bus, to an additional component of the CT system.

14. The circuit of claim 13, wherein the energy storage system comprises an energy storage device coupled to the electrical bus.

15. The circuit of claim 14, wherein the energy storage device is a lithium ion battery.

16. The circuit of claim 14, wherein the energy storage system comprises a buck-boost converter coupled between the energy storage device and the electrical bus.

17. The circuit of claim 13, further comprising a high-voltage generator is coupled to the electrical bus, wherein the high-voltage generator is configured to provide power to an x-ray tube.

18. The circuit of claim 13, wherein the additional component comprises at least one of a data acquisition system (DAQ), a detector cooling fan, and a system control computer, wherein the one or more components are powered by the DC electrical energy converted from the rotational energy in the rotatable base.

19. The CT system of claim 1, wherein the DC bus is configured to pass power to the gantry motor or the energy storage system depending on a mode of operation.

20. The circuit of claim 13, wherein the DC bus is configured to pass power to the gantry motor or the energy storage system depending on a mode of operation.

* * * * *